United States Patent
Muthusamy et al.

(10) Patent No.: US 12,234,246 B2
(45) Date of Patent: Feb. 25, 2025

(54) SOLID STATE FORMS OF BALOXAVIR MARBOXIL

(71) Applicant: ASSIA CHEMICAL INDUSTRIES LTD., Petach Tikva (IL)

(72) Inventors: Anantha Rajmohan Muthusamy, Sivakasi (IN); Amit Singh, Greater Noida (IN); Amol Gulab Khatik, Nagpur (IN); Sundara Lakshmi Kanniah, Greater Noida (IN); Yogesh Dhananjay Wagh, Greater Noida (IN); Parven Kumar Luthra, Thane (IN); Brijnath P. Chaurasia, G.B. Nagar District (IN); Ram Karan Prajapati, Greater Noida (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 804 days.

(21) Appl. No.: 17/435,824

(22) PCT Filed: Mar. 5, 2020

(86) PCT No.: PCT/US2020/021062
§ 371 (c)(1),
(2) Date: Sep. 2, 2021

(87) PCT Pub. No.: WO2020/181025
PCT Pub. Date: Sep. 10, 2020

(65) Prior Publication Data
US 2022/0153753 A1    May 19, 2022

(30) Foreign Application Priority Data

Mar. 5, 2019  (IN) .............................. 201911008540
Mar. 25, 2019 (IN) .............................. 201911011504
Sep. 6, 2019  (IN) .............................. 201911036007
Feb. 7, 2020  (IN) .............................. 202011005438
Feb. 7, 2020  (IN) .............................. 202011005457

(51) Int. Cl.
C07D 498/14    (2006.01)
A61P 31/12     (2006.01)

(52) U.S. Cl.
CPC ............ C07D 498/14 (2013.01); A61P 31/12 (2018.01)

(58) Field of Classification Search
None
See application file for complete search history.

(56) References Cited

U.S. PATENT DOCUMENTS 10,759,814 B2 *  9/2020  Kawai ..................... A61P 31/16

FOREIGN PATENT DOCUMENTS

WO        2018030463 A9    2/2018
WO    WO 2018/030463    *    2/2018  ......... A61K 31/5383

OTHER PUBLICATIONS

Hughes, Organic Process Research & Development (Jun. 21, 2019), 23, pp. 1298-1307.*
Mino R. Caira, "Crystalline Polymorphism of Organic Compounds", Topics In Current Chemistry, vol. 198, pp. 163-208 (1998).
Stephen Byrn, et al., "Pharmaceutical Solids: A Strategic Approach to Regulatory Considerations", Pharmaceutical Research, vol. 12, No. 7, pp. 945-954 (1995).
International Search Report and Written Opinion of the International Searching Authority issued in corresponding application PCT/US2020/021062 mailed Jul. 17, 2020 (18 pages).

* cited by examiner

*Primary Examiner* — Brian J Davis
(74) *Attorney, Agent, or Firm* — Carter, DeLuca & Farrell LLP (57) ABSTRACT

The present disclosure relates to solid state forms of baloxavir marboxil, processes for preparation thereof, pharmaceutical compositions thereof, and methods of use thereof.

18 Claims, 9 Drawing Sheets

Figure 2: XRPD pattern of amorphous baloxavir marboxil

Figure 3: XRPD pattern of Form BM2

Figure 4: XRPD pattern of Form BM3

Figure 6: XRPD pattern of Form BM5

Figure 9: XRPD pattern of Form MS-1 of baloxavir mesylate salt

SOLID STATE FORMS OF BALOXAVIR MARBOXIL

CROSS REFERENCE TO RELATED APPLICATIONS

This application is a National Stage of, and claims priority to and the benefit of, International Patent Application No. PCT/US2020/021062 filed Mar. 5, 2020, which, in turn, claims the benefit of and priority to, Indian Application No. 201911008540, filed Mar. 5, 2019, Indian Application No. 201911011504, filed Mar. 25, 2019, Indian Application No. 201911036007, filed Sep. 6, 2019, Indian Application No. 202011005438, filed Feb. 7, 2020 and Indian Application No. 202011005457, filed Feb. 7, 2020, the entire disclosures of each of which are incorporated by reference herein.

FIELD OF THE INVENTION

The present disclosure relates to salts and solid state forms of baloxavir and baloxavir marboxil, processes for preparation thereof, pharmaceutical compositions thereof, and methods of use thereof.

BACKGROUND

Baloxavir marboxil (compound I), ({(12aR)-12-[(11S)-7,8-difluoro-6,11-dihydrodibenzo[b,e]thiepin-11-yl]-6,8-dioxo-3,4,6,8,12,12ahexahydro-1H-[1,4]oxazino[3,4-c]pyrido[2,1-f][1,2,4]triazin-7-yl}oxy)methyl methyl carbonate, has the following structure:

compound I compound II

Baloxavir marboxil is an antiviral drug developed by Shionogi Co. and Roche for the treatment of influenza A and influenza B infections. It is a prodrug that is converted (by hydrolysis) to baloxavir (compound II), the active form that exerts anti-influenza virus activity.

Baloxavir marboxil is known from WO2016/175224. WO2018/030463 discloses polymorphs of baloxavir marboxil.

WO2017/221869 describes processes for preparation of baloxavir and polymorphs, thereof.

Polymorphism, the occurrence of different crystal forms, is a property of some molecules and molecular complexes. A single compound, like baloxavir marboxil, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts and solid state forms of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and new salts of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of baloxavir and baloxavir marboxil.

SUMMARY OF THE INVENTION

The present disclosure relates to salts and solid state forms of baloxavir and baloxavir marboxil, to processes for preparation thereof, and to pharmaceutical compositions comprising thereof.

In particular, the present disclosure provides crystalline forms of baloxavir marboxil designated as Forms BM1, Form BM2, Form BM3, Form BM4, Form BM5 and Form BM6 (defined herein); crystalline form of baloxavir designated as Form B2 and crystalline form of baloxavir mesylate salt designated as MS-1.

In another aspect, the present disclosure encompasses the above described solid state forms and/or combinations thereof for use in the preparation of pharmaceutical compositions and/or formulations, preferably for use in medicine, preferably for treatment of influenza.

In another aspect, the present disclosure encompasses the use of the above described solid state forms for the preparation of pharmaceutical compositions and/or formulations, preferably for use in medicine, preferably for treatment of influenza.

In yet another embodiment, the present disclosure encompasses pharmaceutical compositions comprising any one or a mixture of the solid states forms of baloxavir and/or baloxavir marboxil.

In a specific embodiment, the present disclosure encompasses pharmaceutical formulations comprising any one of the above described solid state forms and/or combinations thereof and at least one pharmaceutically acceptable excipient.

The present disclosure further encompasses processes to prepare said pharmaceutical formulations, comprising combining any one of the above described solid state forms of baloxavir and/or baloxavir marboxil and/or combinations, or pharmaceutical compositions comprising it, and at least one pharmaceutically acceptable excipient.

The solid state forms as defined herein as well as the pharmaceutical compositions or formulations comprising it can be used as medicaments, particularly for treating influenza, comprising administering a therapeutically effective amount of the solid state forms of the present disclosure, or at least one of the above pharmaceutical compositions or formulations, to a subject suffering from influenza, or otherwise in need of the treatment.

The present disclosure also provides the uses of any one of the above described solid state forms of baloxavir and/or baloxavir marboxil and/or combinations, or at least one of the above pharmaceutical compositions or formulations, for the manufacture of medicaments for treating influenza.

DETAILED DESCRIPTION OF ILLUSTRATIVE EMBODIMENTS

The present disclosure relates to salts and solid state forms of baloxavir and baloxavir marboxil, to processes for preparation thereof and to pharmaceutical compositions comprising these solid state forms.

The solid state forms, according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of baloxavir marboxil, referred to herein as being characterized by graphical data "as depicted in" a Figure will thus be understood to include any crystal form of baloxavir marboxil, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% (w/w) of any other forms of the subject compound as measured, for example, by XRPD. Thus, solid states of baloxavir marboxil described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of baloxavir marboxil. Accordingly, in some embodiments of the disclosure, the described solid state forms of baloxavir marboxil may contain from about 1% to about 20% (w/w), from about 5% to about 20% (w/w), or from about 5% to about 10% (w/w) of one or more other solid state forms of baloxavir marboxil.

In another embodiment, the described solid state form of baloxavir may contain from about 1% to about 20% (w/w), from about 5% to about 20% (w/w), or from about 5% to about 10% (w/w) of one or more other solid state forms of baloxavir.

In another embodiment, the described solid state form MS-1 of baloxavir mesylate salt may contain from about 1% to about 20% (w/w), from about 5% to about 20% (w/w), or from about 5% to about 10% (w/w) of one or more other solid state forms of baloxavir or its salts. Alternatively or additionally, the solid state form MS-1 of baloxavir mesylate salt as described in any embodiment herein may contain: not more than 20%, not more than 10

The present disclosure also comprises a crystalline form of baloxavir marboxil designated as Form BM3. The crystalline Form BM3 of baloxavir marboxil can be characterized by data selected from one or more of the following: an XRPD pattern having peaks at 5.2, 10.1, 15.2, 18.3 and 19.6 degrees 2-theta±0.2 degrees 2-theta; an XRPD pattern substantially as depicted in FIG. 4; or combinations of these data.

Crystalline Form BM3 of baloxavir marboxil may be further characterized by data selected from one or more of the following: an XRPD pattern having peaks at 5.2, 10.1, 15.2, 18.3 and 19.6 degrees two theta±0.2 degrees two theta; and also having one, two, three or four additional peaks selected from 13.4, 22.1, 31.9 and 32.8 degrees two theta±0.2 degrees two theta; or combinations of these data.

Alternatively, crystalline Form BM3 of baloxavir marboxil may be characterized by an XRPD pattern having peaks at: 5.2, 10.1, 13.4, 15.2, 18.3, 19.6, 22.1, 31.9, and 32.8 degrees two theta±0.2 degrees two theta.

Form BM3 of baloxavir marboxil may be a solvated polymorph; preferably, isopropyl acetate solvate, methyl tert-butyl ether solvate, isobutylacetate solvate, or 2-methyl-THF solvate, or may be a solvate with 2-methyl-THF and water.

Thus, in any embodiment of the present invention, Form BM3 of baloxavir marboxil may be a solvate selected from the group consisting of: an isopropyl acetate solvate, a methyl tert-butyl ether solvate, an isobutylacetate solvate, a 2-methyl THF solvate. Alternatively, form BM3 may be an anhydrous form. In an embodiment, Form BM3 of baloxavir marboxil may be an isopropyl acetate solvate. In another embodiment, Form BM3 of baloxavir marboxil may be a methyl tert-butyl ether solvate. In another embodiment, Form BM3 of baloxavir marboxil may be an isobutylacetate solvate. Alternatively, in another embodiment, Form BM3 may be a methyl THF solvate. In another embodiment, Form BM3 may be a mixed solvate with 2-methyl-THF and water.

In a further embodiment, Form BM3 of baloxavir marboxil may be anhydrous form.

In another embodiment the present disclosure comprises a crystalline form of baloxavir marboxil designated as Form BM4. The crystalline Form BM4 of baloxavir marboxil can be characterized by data selected from one or more of the following: an XRPD pattern having peaks at 4.0, 8.2, 9.8, 22.7 and 24.6 degrees 2-theta±0.2 degrees 2-theta; an XRPD pattern substantially as depicted in FIG. 5; or combinations of these data.

Crystalline Form BM4 of baloxavir marboxil may be further characterized by data selected from one or more of the following: an XRPD pattern having peaks at 4.0, 8.2, 9.8, 22.7 and 24.6 degrees two theta±0.2 degrees two theta; and also having one, two, three or four additional peaks selected from 19.1, 20.5, 26.5 and 33.0 degrees two theta±0.2 degrees two theta; or combinations of these data.

Alternatively, crystalline Form BM4 of baloxavir marboxil may be characterized by an XRPD pattern having peaks at: 4.0, 8.2, 9.8, 19.1, 20.5, 22.7, 24.6, 26.5 and 33.0 degrees two theta±0.2 degrees two theta.

Crystalline Form BM4 of baloxavir marboxil may be 1,4-dioxane solvate.

In a further embodiment, the present disclosure comprises a crystalline form of baloxavir marboxil designated as Form BM5. The crystalline Form BM5 of baloxavir marboxil can be characterized by data selected from one or more of the following: an XRPD pattern having peaks at 7.5, 12.2, 18.7, 24.7 and 34.3 degrees 2-theta±0.2 degrees 2-theta; an XRPD pattern substantially as depicted in FIG. 6; or combinations of these data.

Crystalline Form BM5 of baloxavir marboxil may be further characterized by data selected from one or more of the following: an XRPD pattern having peaks at 7.5, 12.2, 18.7, 24.7 and 34.3 degrees two theta±0.2 degrees two theta; and also having one, two, three, four or five additional peaks selected from 13.4, 15.2, 22.9, 26.5 and 31.5 degrees two theta±0.2 degrees two theta; or combinations of these data.

Alternatively, crystalline Form BM5 of baloxavir marboxil may be further characterized by an XRPD pattern having peaks at: 7.5, 12.2, 13.4, 15.2, 18.7, 22.9, 24.7, 26.5, and 34.3 degrees two theta±0.2 degrees two theta.

Crystalline Form BM5 of baloxavir marboxil may be N,N-dimethyl acetamide solvate.

The present disclosure also comprises a crystalline form of baloxavir marboxil designated as Form BM6. The crystalline Form BM6 of baloxavir marboxil can be characterized by data selected from one or more of the following: an XRPD pattern having peaks at 4.0, 8.0, 9.7, 14.7 and 23.2 degrees 2-theta±0.2 degrees 2-theta; an XRPD pattern substantially as depicted in FIG. 7; or combinations of these data.

Crystalline Form BM6 of baloxavir marboxil may be further characterized by data selected from one or more of the following: an XRPD pattern having peaks at 4.0, 8.0, 9.7, 14.7 and 23.2 degrees two theta±0.2 degrees two theta; and also having one, two, three, four or five additional peaks selected from 12.0, 18.0, 20.2, 20.7 and 32.6 degrees two theta±0.2 degrees two theta; or combinations of these data.

Alternatively, crystalline Form BM6 of baloxavir marboxil may be characterized by an XRPD pattern having peaks at: 4.0, 8.0, 9.7, 12.0, 14.7, 18.0, 20.2, 20.7, 23.2 and 32.6 degrees two theta±0.2 degrees two theta.

Crystalline Form BM6 of baloxavir marboxil may be 2-methyl THF solvate.

The present disclosure comprises a crystalline form of baloxavir designated as form B2. The crystalline form B2 of baloxavir can be characterized by data selected from one or more of the following: an XRPD pattern having peaks at 8.7, 11.2, 15.2, 17.7 and 21.7 degrees 2-theta±0.2 degrees 2-theta; an XRPD pattern substantially as depicted in FIG. 8; or combinations of these data.

Crystalline form B2 of baloxavir may be further characterized by data selected from one or more of the following: an XRPD pattern having peaks at 8.7, 11.2, 15.2, 17.7 and 21.7 degrees two theta±0.2 degrees two theta; and also having one, two, three, four or five additional peaks selected from 18.8, 22.3, 25.1, 26.6 and 33.0 degrees two theta±0.2 degrees two theta; or combinations of these data.

Alternatively, crystalline form B2 of baloxavir may be characterized by data an XRPD pattern having peaks at: 8.7, 11.2, 15.2, 17.7, 18.8, 21.7, 22.3, 25.1, 26.6 and 33.0 degrees two theta±0.2 degrees two theta.

In another aspect of the present invention, form B2 of baloxavir is isolated.

In another embodiment, form B2 of baloxavir is anhydrous.

In a further embodiment, the present disclosure comprises a crystalline form of baloxavir mesylate salt designated as form MS-1. The crystalline form MS-1 can be characterized by data selected from one or more of the following: an XRPD pattern having peaks at 7.7, 9.8, 13.8, 16.3 and 26.0 degrees 2-theta±0.2 degrees 2-theta; an XRPD pattern substantially as depicted in FIG. 9; or combinations of these data.

Crystalline form MS-1 of baloxavir mesylate salt may be further characterized by data selected from one or more of the following: an XRPD pattern having peaks at 7.7, 9.8, 13.8, 16.3 and 26.0 degrees two theta±0.2 degrees two theta; and also having one, two, three or four additional peaks selected from 15.6, 18.7, 22.2, 24.3 and 30.7 degrees two theta±0.2 degrees two theta; or combinations of these data.

Alternatively, crystalline form MS-1 of baloxavir mesylate salt may be characterized by an XRPD pattern having peaks at: 7.7, 9.8, 13.8, 15.6, 16.3, 18.7, 22.2, 24.3, 26.0 and 30.7 degrees two theta±0.2 degrees two theta.

Crystalline form MS-1 of baloxavir mesylate salt can be obtained in high purity. In particular, crystalline form MS-1 of baloxavir mesylate can be prepared substantially free of the corresponding R,R-isomer of baloxavir mesylate. For example, the crystalline form MS-1 of baloxavir mesylate as described in any aspect or embodiment, may contain less than 20%, less than 10% or less than 5% of the R,R-isomer of baloxavir mesylate. In embodiments of the invention as described herein where the baloxavir mesylate form MS-1 is used to prepare baloxavir (e.g. baloxavir form B2) or baloxavir marboxil, the baloxavir or baloxavir marboxil can be obtained in high purity, and particularly substantially free (preferably less than 1.0%, less than 0.15% or less than 0.10%) of the corresponding R,R-isomer of baloxavir or of the corresponding R,R-isomer of baloxavir marboxil, respectively. Moreover, in embodiments of the invention where baloxavir mesylate form MS-1 is used to prepare baloxavir marboxil, the product can be obtained in high yield and high purity.

The present disclosure also relates to the crystalline forms of baloxavir and its salt which are obtainable by any of the processes as described herein.

The current novel invention also provides the use of a solid state form of the present disclosure (preferably form B2 baloxavir, or form MS-1 of baloxavir mesylate) for preparing baloxavir marboxil (any method known in the art can be used; (e.g., example 4 of US2018/0118760)).

As described above, depending on which other solid state it is compared with, the polymorphs of baloxavir marboxil or baloxavir, or baloxavir mesylate according to the present disclosure may have advantageous properties as described above.

The present disclosure also relates to the crystalline forms of baloxavir marboxil, or baloxavir mesylate which are obtainable by any of the processes as described herein.

The present invention also provides the use of any one of the solid state forms of baloxavir marboxil for preparing other solid state forms of baloxavir marboxil. Particularly, the present invention provides the use of any one of the solid state forms of baloxavir marboxil as described in any embodiment herein, preferably form BM3, for the preparation of amorphous baloxavir marboxil.

The present disclosure also relates to a pharmaceutical composition comprising any one of or a mixture of the solid state forms of baloxavir marboxil according to the present invention.

The invention further comprises a process for preparing said pharmaceutical compositions of baloxavir marboxil, wherein the process comprises combining any one of the above solid state forms and/or combinations thereof with at least one pharmaceutically acceptable excipient.

In another aspect, the present disclosure encompasses the above described solid state forms of baloxavir marboxil and/or combinations thereof for use in the preparation of pharmaceutical compositions and/or formulations, preferably for use in medicine, preferably for treating Influenza.

In another aspect, the present disclosure encompasses the use of any one of the above described solid state forms of baloxavir marboxil and/or combinations thereof for the preparation of pharmaceutical compositions and/or formulations, preferably for use in medicine, preferably for the treatment of patients suffering from Influenza.

In yet another embodiment, the present disclosure encompasses pharmaceutical compositions comprising any one of the above described solid state forms of baloxavir marboxil and/or combinations thereof.

In a specific embodiment, the present disclosure encompasses pharmaceutical formulation comprising any one of the above described solid state forms of baloxavir marboxil and/or combinations thereof, and at least one pharmaceutically acceptable excipient.

The present disclosure further encompasses processes to prepare said pharmaceutical formulations of baloxavir marboxil, comprising combining the above described solid state forms of baloxavir marboxil, or pharmaceutical compositions comprising them, and at least one pharmaceutically acceptable excipient.

The present disclosure comprises processes for preparing the above mentioned pharmaceutical compositions. The processes comprise combining the above described crystalline polymorphs of baloxavir marboxil and/or combinations thereof with at least one pharmaceutically acceptable excipient.

Pharmaceutical formulations of the present invention contain any one of the crystalline polymorphs of baloxavir marboxil of the present invention and/or combinations thereof. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, baloxavir marboxil and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

The present invention also provides a process for preparing baloxavir marboxil, or for preparing other solid state forms of baloxavir marboxil, particularly forms BM1, BM2, BM3, BM4, BM5, BM6 or amorphous form of baloxavir marboxil, as described in any embodiment herein, and especially form BM3 of baloxavir marboxil as described in any embodiment herein, using Form B2 of baloxavir. The process can be according to any method in the art. For example: The process may comprise reacting Form B2 of baloxavir with, for example, a compound of formula: L-CH$_2$O—C(=O)OMe, where L is a leaving group such as Cl, OTs and OMs. Particularly, Form B2 of baloxavir may be reacted with chloromethyl methyl carbonate. In any embodiment, the reaction may be conducted in any suitable solvent, such as for example a polar aprotic solvent. In any embodiment the reaction may be conducted in the presence of a base, such as an inorganic base (for example, an alkali metal carbonate such as sodium carbonate or potassium carbonate). In any embodiment, the reaction may be carried out in the presence of a catalyst (e.g. a nucleophile, such as iodide or bromide ions; particularly an alkali metal iodide or an alkali metal bromide, such as potassium iodide, sodium iodide, potassium bromide or sodium bromide. The process may further comprise combining the resulting baloxavir marboxil or solid state form of baloxavir marboxil, particularly form BM3, with at least one pharmaceutically acceptable excipient to form a pharmaceutical composition or formulation.

In another embodiment, form BM3 may be converted into another solid state form of baloxavir marboxil, particularly amorphous baloxavir marboxil. In embodiments, the resulting amorphous baloxavir marboxil can be combined with at least one pharmaceutically acceptable excipient to form a pharmaceutical composition or formulation comprising amorphous baloxavir marboxil. Form BM3 of baloxavir marboxil is preferably converted to amorphous baloxavir marboxil by a process comprising solvent removal from a solution of Form BM3 in an organic solvent, preferably wherein the solvent removal comprises spray drying. Suitable solvents include dichloromethane, acetone, methanol, isopropylacetate, ethyl acetate, or mixtures thereof. Preferably, the solvent is dichloromethane. The amorphous baloxavir marboxil prepared according to the above process may be stable; e.g., stable to conversion to other solid state forms, and more suitable for tableting.

The invention further comprises the use of Form B2 of baloxavir for preparing baloxavir marboxil, or for preparing other solid state forms of baloxavir marboxil, particularly forms BM1, BM2, BM3, BM4, BM5, BM6, or amorphous form of baloxavir marboxil, as described in any embodiment herein, and especially form BM3 of baloxavir marboxil as described in any embodiment herein, or amorphous form of baloxavir marboxil. The invention further comprises the use of Form B2 of baloxavir for preparing a pharmaceutical composition or pharmaceutical composition comprising: baloxavir marboxil, other solid state forms of baloxavir marboxil, particularly forms BM1, BM2, BM3, BM4, BM5, BM6, or amorphous form of baloxavir marboxil, and especially a pharmaceutical composition or a pharmaceutical formulation comprising: form BM3 of baloxavir marboxil or amorphous form of baloxavir marboxil.

The present invention further comprises a process for the preparation of baloxavir mesylate, or a salt or solid state form of baloxavir mesylate particularly form MS-1 of baloxavir mesylate as described in any embodiment herein, using baloxavir. The process may comprise reacting baloxavir with methane sulfonic acid in a suitable solvent. In any embodiment, baloxavir is reacted with methane sulfonic acid in acetonitrile. The resulting baloxavir mesylate, particularly Form MS-1 may be converted to baloxavir (particularly baloxavir form B2 or to baloxavir marboxil or a solid state form of baloxavir marboxil. For the preparation of baloxavir marboxil, the process may comprise reacting baloxavir mesylate, particularly Form MS-1 of baloxavir mesylate as described in any embodiment herein with, for example, a compound of formula: L-CH$_2$O—C(=O)OMe, where L is a leaving group such as Cl, OTs and OMs. Particularly, the baloxavir mesylate may be reacted with chloromethyl methyl carbonate. In any embodiment, the reaction may be conducted in any suitable solvent, such as for example a polar aprotic solvent. In any embodiment the reaction may be conducted in the presence of a base, such as an inorganic base (for example, an alkali metal carbonate such as sodium carbonate or potassium carbonate). In any embodiment, the reaction may be carried out in the presence of a catalyst (e.g. a nucleophile, such as iodide or bromide ions; particularly an alkali metal iodide or an alkali metal bromide, such as potassium iodide, sodium iodide, potassium bromide or sodium bromide.

In embodiments where the baloxavir mesylate form MS-1 is converted to baloxavir marboxil, as described above, the process can further comprise combining the baloxavir marboxil with at least one pharmaceutically acceptable excipient to form a pharmaceutical composition or formulation.

In embodiments, form BM3 of baloxavir marboxil may be converted to amorphous baloxavir marboxil. The resulting amorphous baloxavir marboxil may be combined with at least one pharmaceutically acceptable excipient to form a pharmaceutical composition or formulation.

The present invention additionally provides the use of baloxavir mesylate forms MS-1 for preparing baloxavir Form B2 baloxavir.

The present invention further provides the use of baloxavir mesylate, particularly Form MS-1 baloxavir mesylate, for the preparation of baloxavir marboxil or a solid state form of baloxavir marboxil.

The present invention further comprises a process for preparing baloxavir, preferably Form B2 of baloxavir, using baloxavir mesylate form MS-1 as described in any embodiment herein. Preferably, the invention comprises reacting baloxavir mesylate form MS-1 as described in any embodiment herein, with a base. The base is preferably an alkali metal carbonate or an alkali metal bicarbonate. Particularly the base is an alkali metal bicarbonate, especially sodium bicarbonate. The reaction may be carried out in any suitable solvent, such as water. The present invention further provides the use of form MS-1 baloxavir mesylate for preparing a pharmaceutical composition or a pharmaceutical formulation comprising: baloxavir marboxil, other solid state forms of baloxavir marboxil, particularly forms BM1, BM2, BM3, BM4, BM5, BM6, or amorphous form of baloxavir marboxil, and especially a pharmaceutical composition or a pharmaceutical formulation comprising: form BM3 of baloxavir marboxil or amorphous form of baloxavir marboxil.

Baloxavir mesylate, preferably form MS-1, may also be prepared by deprotecting 7-protected baloxavir (e.g. 7-benzyloxy protected baloxavir by reaction with magnesium chloride in an aprotic solvent (preferably dimethyl acetamide) to form baloxavir, and reacting the baloxavir with methane sulfonic acid, preferably in an aprotic solvent (preferably dichloromethane) to form baloxavir mesylate. The deprotection and reaction with methane sulfonic acid can be carried out without isolation of baloxavir as an intermediate, or can be carried out with isolation of baloxavir. Optionally, the resulting baloxavir mesylate may be converted to baloxavir marboxil as described above. The process may further comprise combining the resulting baloxavir marboxil with at least one pharmaceutically acceptable excipient to prepare a pharmaceutical composition or pharmaceutical formulation.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-ray diffraction was performed on X-Ray powder diffractometer:

Bruker D8 Advance; Copper Kα radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement parameters:

Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

All X-Ray Powder Diffraction peak values are calibrated with regard to standard silicon spiking in the sample.

Procedure for Modulated Differential Scanning Calorimetry (mDSC):

mDSC was performed using a TA instrument Q2000 differential scanning Calorimetry. About 3-5 mg sample was accurately weighed into an aluminum pan, and covered with a lid having hole and then crimped. The sample cell was heated at a rate of 3° C./min up to 200° C. under the nitrogen atmosphere with amplitude of 1° C. and Modulation 60 sec·m.

EXAMPLES

Polymorphs type I and III of baloxavir marboxil can be obtained by any method known in the literature (e.g., WO2018/030463).

Example 1

Preparation of Baloxavir Marboxil Form BM1

Figure 1:
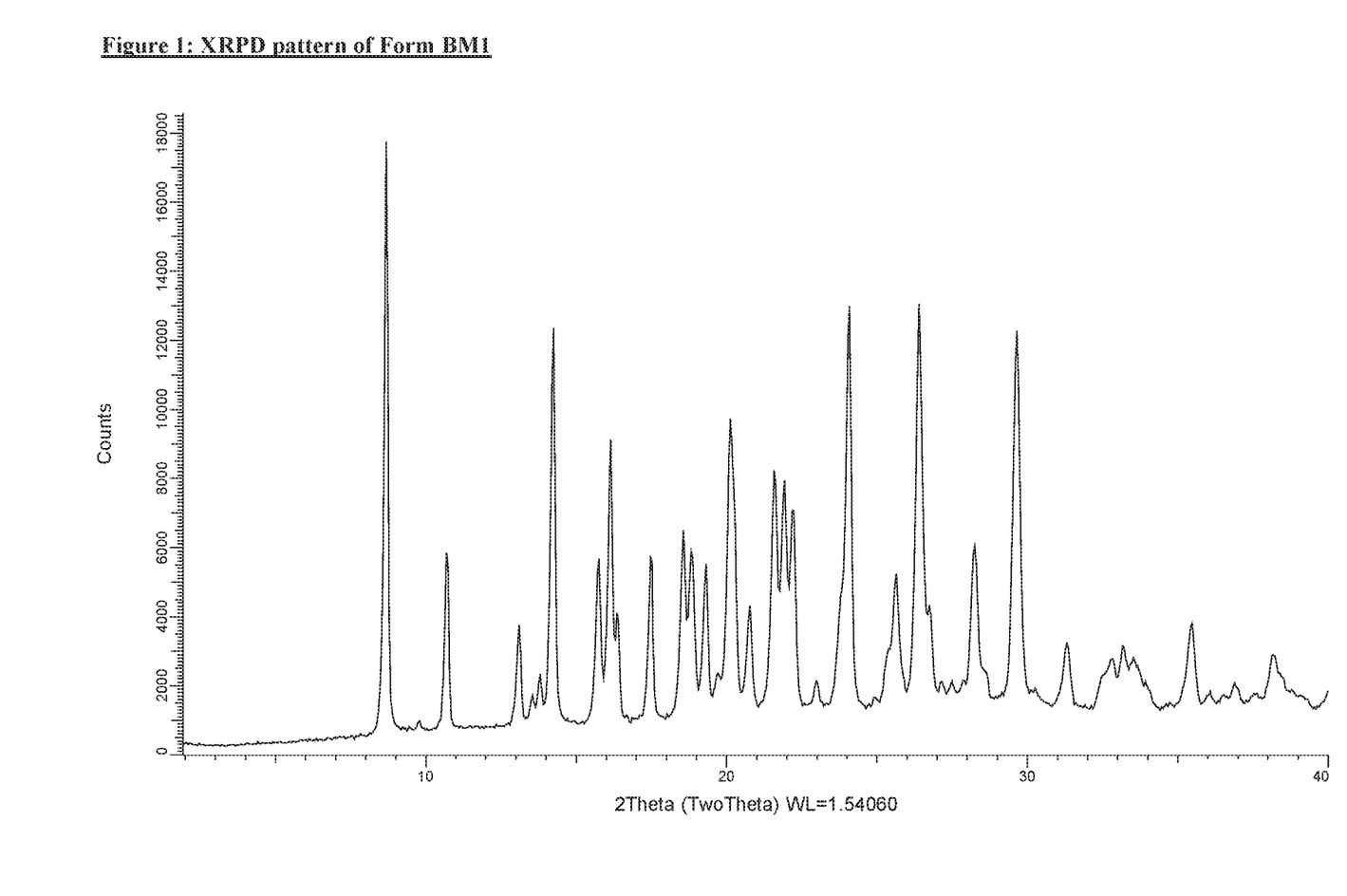
FIG. 1 shows an X-ray powder diffraction (XRPD) pattern of baloxavir marboxil Form BM1.

Baloxavir marboxil (type III, 0.05 g) was dissolved in dichloromethane (0.25 mL) at 40-45° C. and filtered through 0.45 micron filter to remove any undissolved particulates. The clear solution was subjected to fast evaporation under reduced pressure (below 50 mbar) at 40-45° C. After complete distillation, the obtained solid was analyzed by XRPD and designated as Baloxavir marboxil Form BM1; as shown in FIG. 1.

Example 2

Preparation of Baloxavir Marboxil Form BM1

Baloxavir marboxil (type III, 0.05 g) was dissolved in methanol (2.0 mL) at 55-60° C. and filtered through 0.45 micron filter to remove any undissolved particulate. The clear solution was kept under magnetic stirring (about 500 rpm) and water was slowly added (10.0 mL) in 5-10 minutes at 55-60° C. The reaction mixture was cooled down to 25-30° C. in about 30 minutes under stirring. Reaction mixture was maintained under stirring for 24 hours at 25-30° C. After 24 hours, the reaction mass was filtered and residue was washed with water (5 mL×2). The obtained solid was dried under vacuum (15-20 minutes) and characterized by X-ray powder diffractogram ("XRPD") to give baloxavir marboxil Form BM1.

Example 3

Baloxavir Marboxil Amorphous

Figure 2:
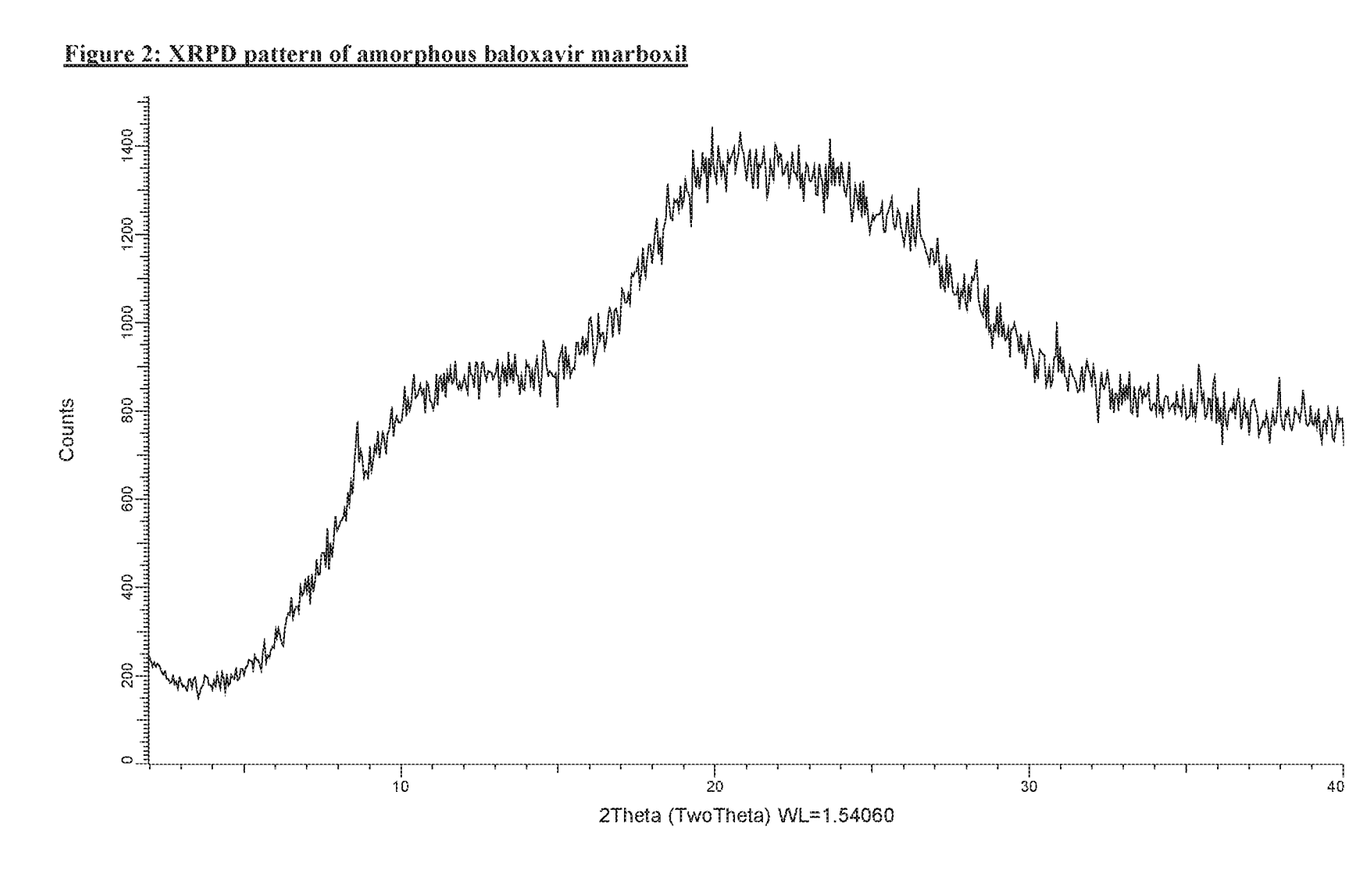
FIG. 2 shows an X-ray powder diffraction (XRPD) pattern of amorphous baloxavir marboxil.

Baloxavir Marboxil (type III, 0.1 g) was dissolved in acetic acid (2 mL) at 55-60° C. in a round bottom flask and obtained clear solution. The clear solution was subjected to distillation under reduced pressure at 55-60° C. Solid material was obtained and isolated at 22-25° C. The obtained solid was characterized by X-ray powder diffractogram to give amorphous baloxavir marboxil; as shown in FIG. 2.

Example 4

Preparation of Baloxavir Marboxil Form BM2

Figure 3:
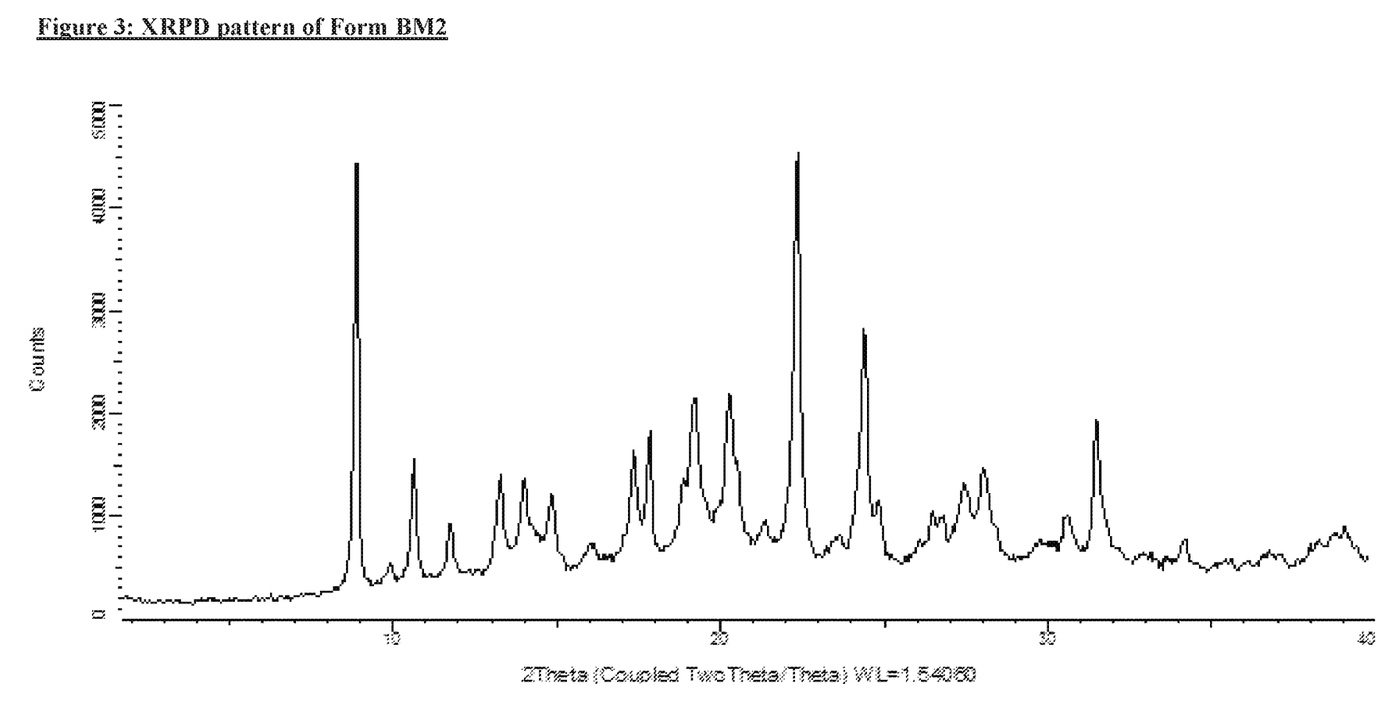
FIG. 3 shows an X-ray powder diffraction (XRPD) pattern of baloxavir marboxil Form BM2.

Baloxavir marboxil (Amorphous, 0.1 g) was dissolved in chloroform (0.5 mL) in a sealed vial. The reaction mass was heated up to 70° C. (1° C./minute) and stirred at 70° C. for 10 minutes, then cooled down to −20° C. (1° C./min) and maintained for 15 minutes. After repeating the temperature cycling twice, the reaction mass was brought to 22-25° C. The solid material was filtered, sucked for about 15 minutes and then dried under nitrogen atmosphere at 160° C. for about 10 minutes. The obtained solid was analyzed by XRPD to give baloxavir marboxil Form BM2; as shown in FIG. 3.

Example 5

Preparation of Baloxavir Marboxil Form BM3

Figure 4:
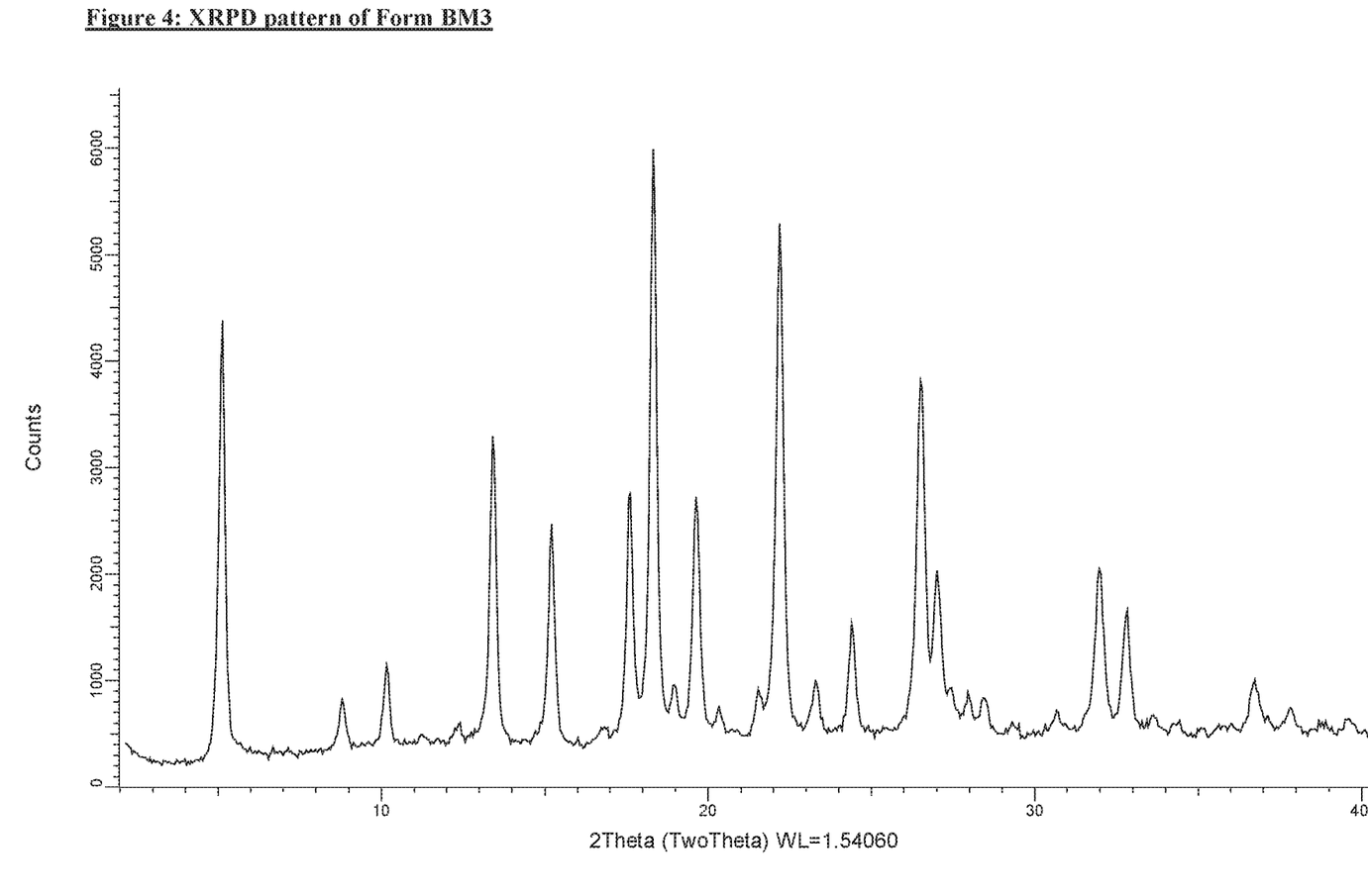
FIG. 4 shows an X-ray powder diffraction (XRPD) pattern of baloxavir marboxil Form BM3.

Baloxavir marboxil (type III, 0.05 g) was dissolved in isopropyl acetate (8 mL) at 60-65° C. and filtered through 0.45 micron filter to remove any undissolved particulates. The clear solution was slowly cooled down to 22-25° C. and kept under magnetic stirring for 24 hours. The obtained solid was filtered, dried under vacuum for 15-20 minutes and analyzed by XRPD to give baloxavir marboxil Form BM3 (FIG. 4).

Example 6

Preparation of Baloxavir Marboxil Form BM4

Figure 5:
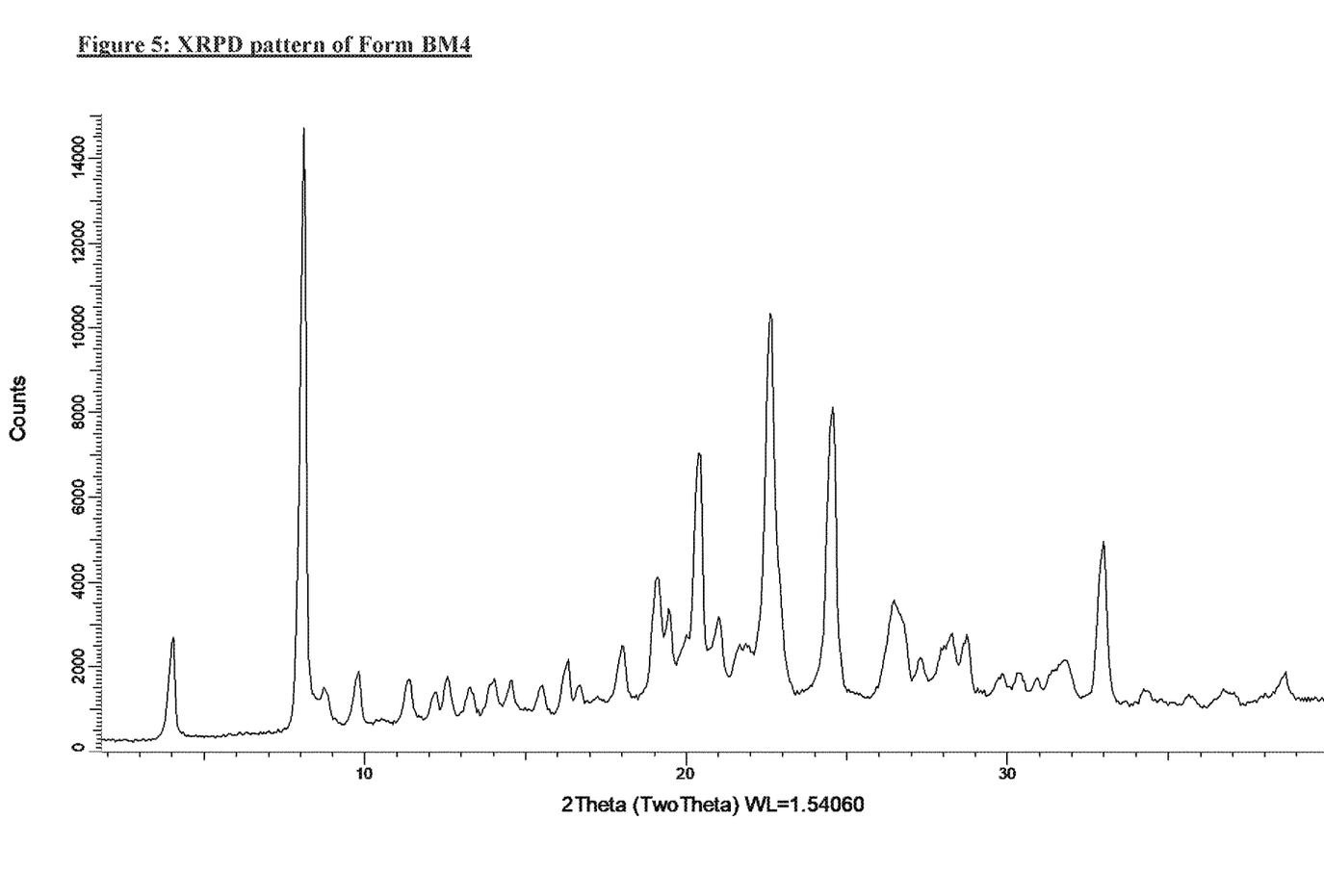
FIG. 5 shows an X-ray powder diffraction (XRPD) pattern of baloxavir marboxil Form BM4.

Baloxavir marboxil (Amorphous, 0.07 g) and 1, 4-dioxane (1 mL) were placed in a glass vial (5 mL) at 22-25° C. The slurry mass was heated up to 60° C. and stirred (magnetic stirrer, 500 RPM) for 24 hours. The slurry was filtered, dried under vacuum for 15-20 minutes and analyzed by XRPD—baloxavir marboxil Form BM4 was obtained, as shown in FIG. 5.

Example 7

Preparation of Baloxavir Marboxil Form BM5

Figure 6:
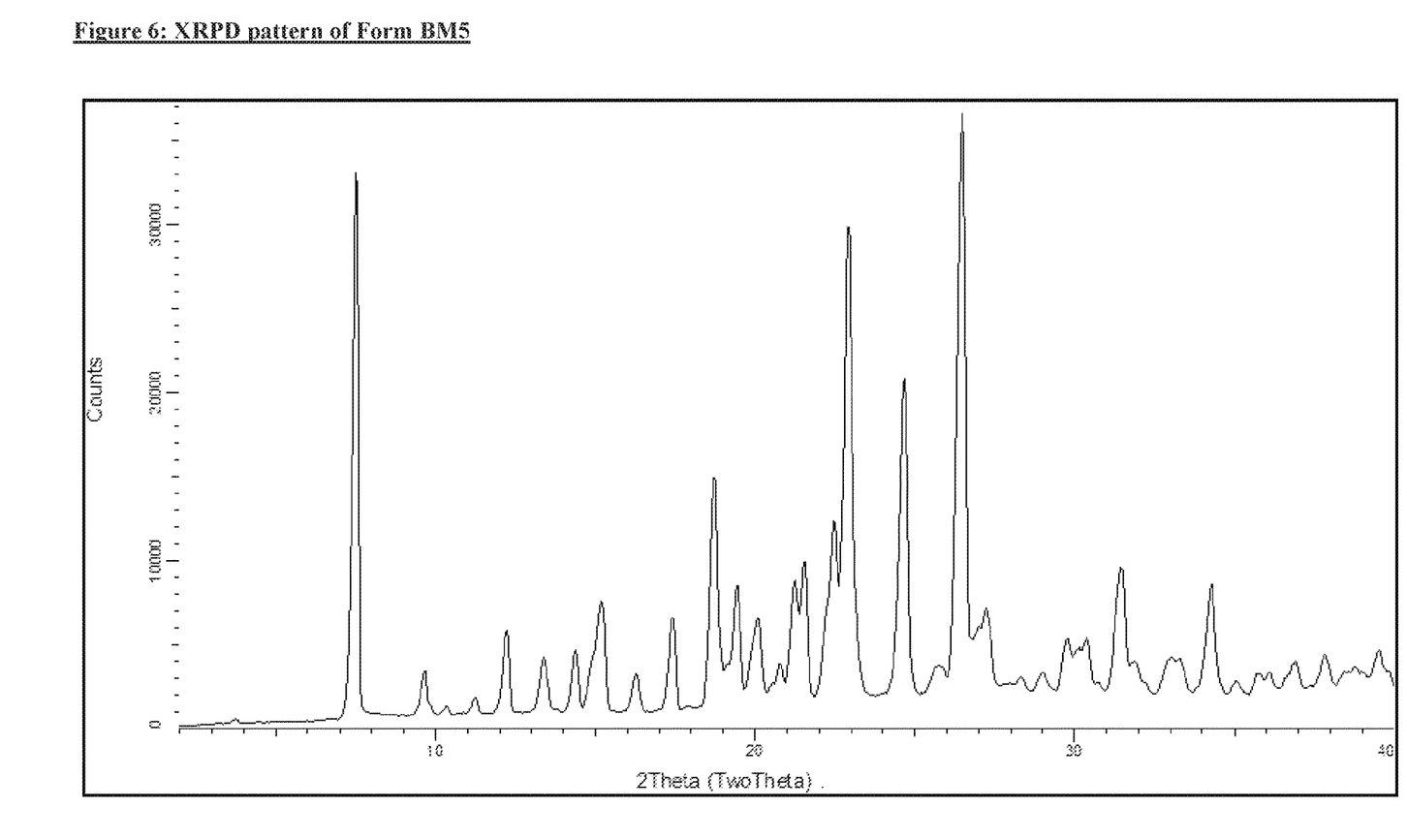
FIG. 6 shows an X-ray powder diffraction (XRPD) pattern of baloxavir marboxil Form BM5.

Baloxavir Marboxil (amorphous, 0.1 g) was dissolved in N,N-Dimethyl acetamide (0.8 mL) at 60° C. The solution was filtered through 0.45 micron filter, water (0.4 ml) was added to the clear solution and the vial was sealed. The clear solution was heated to 70° C. in 30 minutes and maintained for 3 hours at 70° C. then cooled down to −20° C. in 5 hours and maintained at −20° C. for 5 h. The obtained slurry was heated again to 70° C. in 30 minutes and maintained for 3 hours at 70° C. then cooled down to −20° C. in 5 hours and maintained at −20° C. for 5 hours under magnetic stirring (300 rpm). The slurry was finally filtered in cool temperature (−20° C.), suck dried under vacuum for 15-20 minutes and analyzed by XRPD-baloxavir marboxil Form BM5 was obtained, as shown in FIG. 6.

Example 8

Preparation of Baloxavir Marboxil Form BM6

Figure 7:
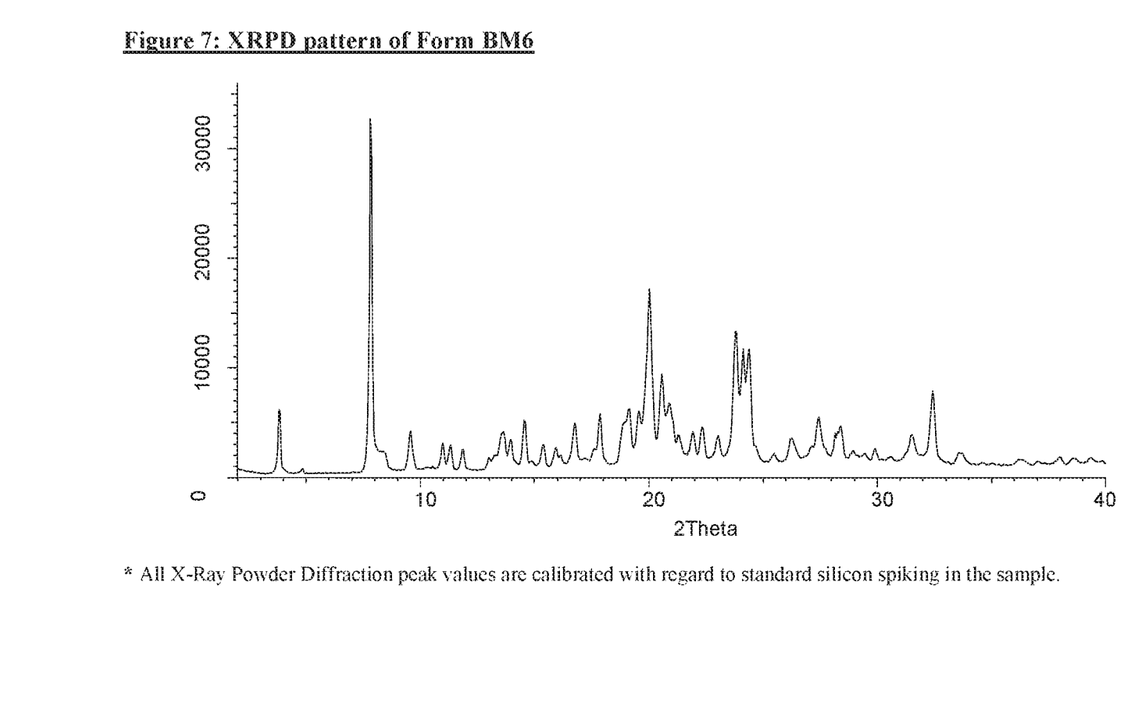
FIG. 7 shows an X-ray powder diffraction (XRPD) pattern of baloxavir marboxil Form BM6.

Baloxavir marboxil (type I; 5 g) and 2-Methyl THF (800 mL) were taken in a flask at 22-25° C. The flask was heated to 70° C. and maintained at 70° C. for 1hr to obtain a clear solution. The solvent was evaporated (at 50° C.) up to 350 mL. The obtained slurry further stirred at 0-5° C. for 90 min. The obtained solid was filtered under vacuum at 0-5° C. and kept for suction for 30 minutes at 22-25° C.The obtained material was analyzed by XRPD-baloxavir marboxil Form BM6; as shown in FIG. 7.

Example 9

Preparation of Baloxavir Marboxil Amorphous

Baloxavir marboxil (Form BM3, 5 g) was dissolved in dichloromethane (50 mL) at room temperature, filtered through a hyflow bed and the hyflow bed was washed with dichloromethane (30 ml). The clear solution was subjected to spray drying by using Buchi B-290 mini spray dryer with aspiration 100%, Feed inlet temperature: 54±6° C.; Outlet temperature: 48±1° C. and feed rate of 2.2 ml per minute. The obtained solid was amorphous form of baloxavir marboxil with glass transition (Tg) at about 115.8° C.

Example 10

Preparation of Baloxavir Marboxil Form BM3

Baloxavir marboxil (amorphous, 1 g) was dissolved in methanol (25 ml) at 45-50° C. The solution was filtered through 0.45 micron filter, pre-cooled methyl tert butyl ether (MTBE, 125 ml) was added at 0° C. and the reaction mass was stirred at 0° C. for 16-18 hours. The reaction mass was brought to room temperature, filtered and dried (suction) for 15-30 minutes. Solid was then dried in vacuum oven at 60° C. for 4 hours. The obtained solid was analyzed by XRPD-Form BM3.

Example 11

Preparation of Baloxavir Marboxil Form BM3

Baloxavir marboxil (type I, 0.1 g) was taken into a 25 ml test tube. A mixture of 2-Methyl THF:Water (1:1; 3 ml) was added and the reaction mixture was heated to 60° C. and maintained for 1 h. The clear solution was cooled to 0-5° C. and stirred at 0-5° C. for 20 hours. The obtained solid was filtered under vacuum at 0-5° C. and kept for suction for 5 minutes at room temperature. The obtained material (0.05 g) was analyzed by XRPD-Form BM3.

Example 12

Preparation of Mesylate Salt of Baloxavir (MS-1)

Figure 9:
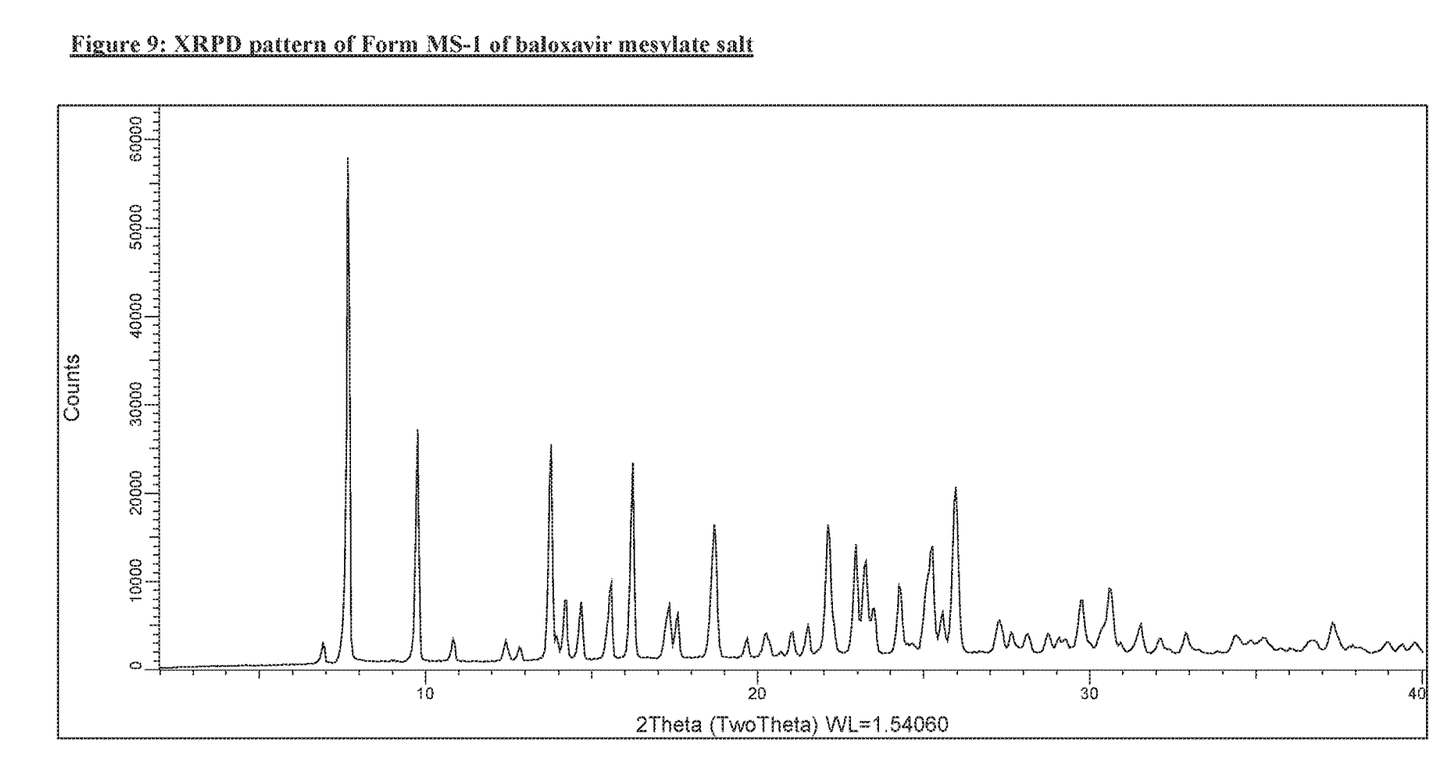
FIG. 9 shows an X-ray powder diffraction (XRPD) pattern of Form MS-1 of baloxavir mesylate salt.

Baloxavir (5.0 g) and acetonitrile (50 ml) were charged in a vessel, the temperature was raised to 60-70° C. and methane sulfonic acid (1.0 g) was added over 5 to 10 minutes. Resultant reaction mixture was stirred at 60-70° C. for 0.5 hour. The mixture was slowly cooled to 30-40° C. and maintained for additional hour with stirring. The obtained solid was filtered and dried under vacuum (15-30 minutes). The crude material was washed with ethanol and dried under vacuum at 60° C. to obtain the mesylate salt of baloxavir (3.7 g). The obtained solid was analyzed by XRPD and designated as MS-1; as shown in FIG. 9.

Example 13

Preparation of Form B2 of Baloxavir

Figure 8:
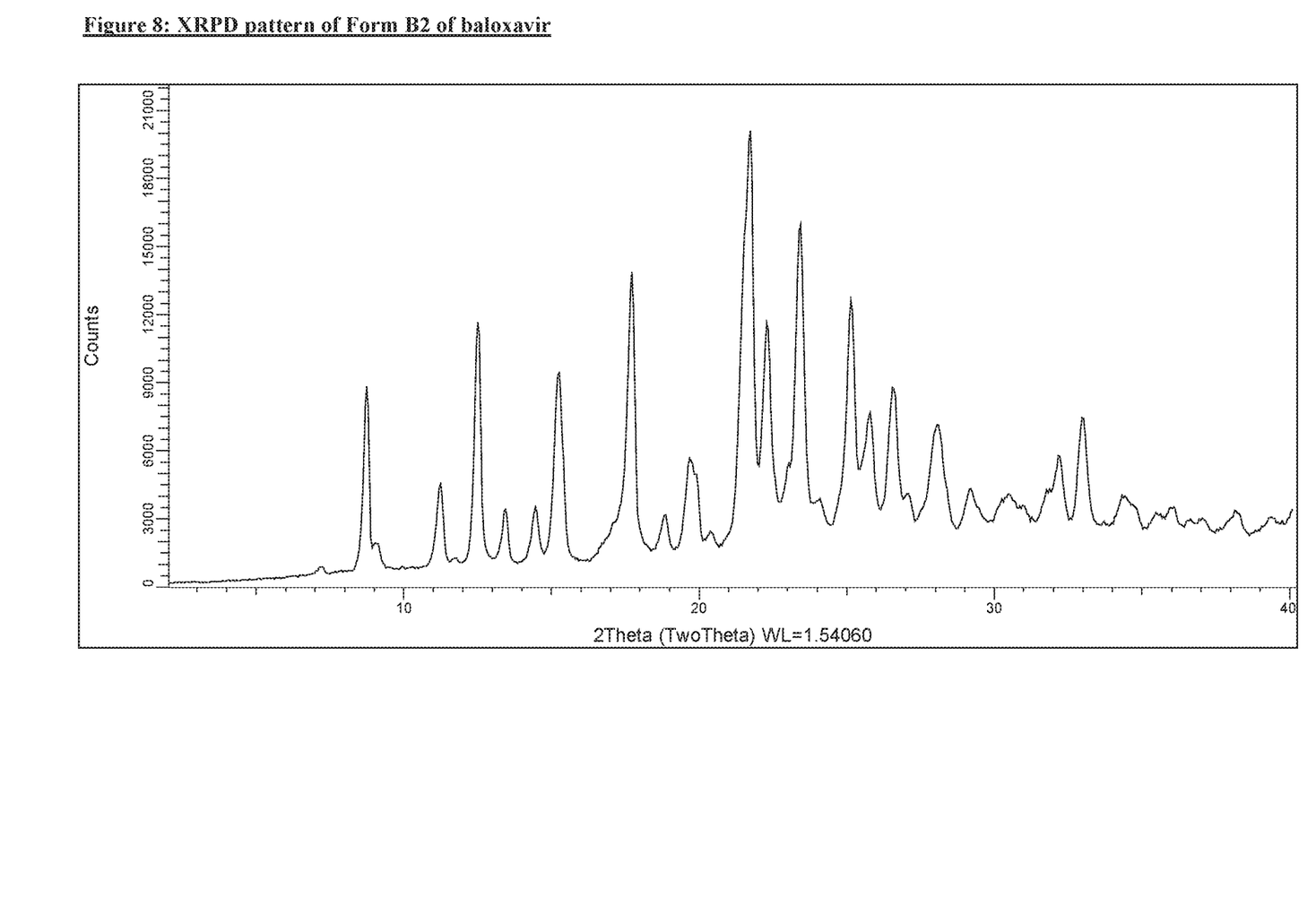
FIG. 8 shows an X-ray powder diffraction (XRPD) pattern of Form B2 of baloxavir.

Baloxavir mesylate salt (MS-1, 4.0 g) and doubly ionized water (12 mL) were charged in a vessel. The reaction mixture was heated to 35-40° C. An aqueous sodium bicarbonate solution (5%) was slowly added and pH adjusted to 6-7 at 35-40° C. The reaction mixture was cooled to 25-30° C. and stirred for an additional hour. The obtained solid was filtered and dried under vacuum (for 15-30 minutes) and then washed with water (4 mL). The compound was dried under vacuum at 60° C. for 6-8 hours to obtain form B2 of baloxavir (3.0 g); as shown in FIG. 8.

Example 14

Preparation of Mesylate Salt of Baloxavir (MS-1)

To a solution of (R)-7-(benzyloxy)-12-((S)-7,8-difluoro-6,11-dihydrodibenzo[b,e]thiepin-11-yl)-3,4,12,12a-tetrahydro-1H-[1,4]oxazino[3,4-c]pyrido[2,1-f][1,2,4]triazine-6,8-dione (8 g) in Dimethyl acetamide (24 ml) was added magnesium chloride (1.99 g) at 20-30° C. Temperature was raised to 65-70° C. and the reaction mixture was stirred during 3-4 hours. The reaction mixture was cooled to 20-25° C. followed by addition of 0.5N aqueous HCl (80 ml) and dichloromethane (80 ml). The obtained mixture was stirred for 1-2 hours at 20-30° C., layers were separated, and the organic layer was washed with water (40 ml) and concentrated under vacuum leaving about 50-60 ml of concentrated mass. To the above mass, containing baloxavir free base was added methane sulfonic acid (1.28 g). Resultant reaction mixture was stirred for 1-2 hours at 20-30° C. The obtained solid was filtered, washed with dichloromethane (16 ml), and dried under vacuum at 60° C. to obtain form MS-1 of baloxavir mesylate salt (4.4 g).

Example 15

Preparation of Baloxavir Marboxil

Mesylate salt of baloxavir (MS-1) (10 gm 0.0172 mole), N,N-Dimethyl acetamide (50 ml), potassium carbonate (3.58 gm 0.026 mole), potassium iodide (2.86 gm 0.0172 mole) and chloromethyl methyl carbonate (3.22 gm 0.026 mole) were stirred under nitrogen atmosphere at 20° C. to 30° C. The reaction mixture was heated to 45° C. to 55° C. and stirred about 1 hour. Additional portion of potassium carbonate (2.39 gm 0.0172 mole) and chloromethyl methyl carbonate (0.54 gm 0.0043 mol) were added at 45° C. to 55° C. and the reaction mixture was stirred for about 1 hour. Once again, potassium carbonate (1.193 gm 0.0086 mole) and chloromethyl methyl carbonate (0.54 gm 0.0043 mole) were added and the reaction mixture was stirred for 1 to 2 hours at 45° C. to 55° C. After the reaction was completed, the reaction mass was cooled to room temperature and acetone (15 ml) was added. The reaction mixture was further cooled to 0° C. to 10° C., acetic acid (15 ml) was added and temperature was raised to room temperature and water (100 ml) was added slowly. The reaction mixture was stirred for 2 hours to 4 hours and filtered. The obtained wet cake was washed with a mixture of acetone: water (1:4, 20 ml) followed by wash with water (20 ml). The obtained material was dried under vacuum at 60° C. to 70° C. to obtain baloxavir marboxil (7 g).

The invention claimed is:

1. A crystalline form of baloxavir marboxil designated as Form BM3, characterized by data selected from one or more of the following:
  an XRPD pattern having peaks at: 5.2, 10.1, 15.2, 18.3 and 19.6 degrees 2-theta±0.2 degrees 2-theta;
  an XRPD pattern substantially as depicted in FIG. 4; or combinations of these data.

2. The crystalline Form BM3 of baloxavir marboxil according to claim 1, wherein said crystalline Form BM3 is characterized by having one, two, three or four additional peaks selected from 13.4, 22.1, 31.9 and 32.8 degrees two theta±0.2 degrees two theta.

3. The crystalline Form BM3 of baloxavir marboxil according to claim 1, characterized by an XRPD having peaks at: 5.2, 10.1, 13.4, 15.2, 18.3, 19.6, 22.1, 31.9 and 32.8 degrees 2-theta±0.2 degrees 2-theta.

4. The crystalline Form BM3 according to claim 1; wherein said form is a solvated form.

5. The crystalline Form BM3 according to claim 4, wherein Form BM3 is isopropyl acetate solvate, methyl tert-butyl ether solvate, isobutylacetate solvate, or 2-methyl-THF solvate, or may be a solvate with 2-methyl-THF and water.

6. The crystalline Form BM3 according to claim 1, wherein said form is an anhydrous form.

7. A process for preparing a second solid state form of baloxavir marboxil or salts thereof, comprising:
  preparing Form BM3 of baloxavir marboxil as defined in claim 1; and
  converting Form BM3 of baloxavir marboxil to the second solid state form or salt of baloxavir marboxil, wherein converting includes:
    dissolving Form BM3 of baloxavir marboxil in a solvent to form a solution; and
    removing the solvent from the solution to form the second solid state forms of baloxavir marboxil or salts thereof.

8. The process of claim 7, comprising converting Form BM3 of baloxavir marboxil to amorphous baloxavir marboxil by removing the solvent from the solution using spray drying.

9. The process according to claim 7, further comprising removing solvent from a solution of Form BM3 in an organic solvent.

10. A process according to claim 9, wherein the solvent is selected from dichloromethane, acetone, methanol, isopropylacetate, ethyl acetate or mixture thereof.

11. A process according to claim 7, further comprising combining the solid state form or salt of baloxavir marboxil with at least one pharmaceutically acceptable excipient to form a pharmaceutical composition or formulation.

12. A pharmaceutical composition comprising Form BM3 of baloxavir marboxil as defined in claim 1.

13. A pharmaceutical formulation comprising Form BM3 of baloxavir marboxil as defined in claim 1, and at least one pharmaceutically acceptable excipient.

14. A process for preparing a pharmaceutical formulation comprising:
  combining the crystalline Form BM3 of baloxavir marboxil as defined in claim 1, with at least one pharmaceutical acceptable excipient.

15. A method of treating influenza comprising administering to a subject suffering from influenza a therapeutically effective amount of the crystalline From BM3 of baloxavir marboxil as defined in claim 1.

16. A crystalline form of baloxavir mesylate salt designated as Form MS-1, characterized by data selected from one or more of the following:
  an XRPD pattern having peaks at 7.7, 9.8, 13.8, 16.3 and 26.0 degrees 2-theta±0.2 degrees 2-theta;
  an XRPD pattern substantially as depicted in FIG. 9; or combinations of these data.

17. The crystalline Form MS-1 of baloxavir mesylate salt according to claim 16, wherein said crystalline Form MS-1 is further characterized by an XRPD pattern having one, two, three or four additional peaks selected from 15.6, 18.7, 22.2, 24.3 and 30.7 degrees 2-theta±0.2 degrees 2-theta.

18. The crystalline Form MS-1 of baloxavir mesylate salt according to claim 16, which is characterized by an XRPD pattern having peaks at: 7.7, 9.8, 13.8, 15.6, 16.3, 18.7, 22.2, 24.3, 26.0 and 30.7 degrees 2-theta±0.2 degrees 2-theta.

* * * * *